(12) United States Patent
Schwemberger et al.

(10) Patent No.: US 6,589,200 B1
(45) Date of Patent: *Jul. 8, 2003

(54) ARTICULATING ULTRASONIC SURGICAL SHEARS

(75) Inventors: Richard F. Schwemberger, Cincinnati, OH (US); John C. Wright, Loveland, OH (US)

(73) Assignee: Ethicon Endo-Surgery, Inc., Cincinnati, OH (US)

(*) Notice: Subject to any disclaimer, the term of this patent is extended or adjusted under 35 U.S.C. 154(b) by 0 days.

This patent is subject to a terminal disclaimer.

(21) Appl. No.: 09/464,973

(22) Filed: Dec. 16, 1999

Related U.S. Application Data

(63) Continuation-in-part of application No. 09/255,519, filed on Feb. 22, 1999, now Pat. No. 6,090,120.

(51) Int. Cl.$^7$ .............................. A61B 17/20; A61B 8/12
(52) U.S. Cl. ...................... 604/22; 600/459; 606/169
(58) Field of Search ....................... 606/1, 169, 170, 606/171, 205–210; 604/22; 600/439

(56) References Cited

U.S. PATENT DOCUMENTS

| | | |
|---|---|---|
| 2,990,616 A | 7/1961 | Balamuth et al. |
| 3,053,124 A | 9/1962 | Balamuth et al. |
| 4,108,211 A | 8/1978 | Tanaka |
| 5,058,570 A | 10/1991 | Idemoto et al. |
| 5,203,338 A | 4/1993 | Jang |
| 5,275,166 A | 1/1994 | Vaitekunas et al. |
| 5,322,055 A | 6/1994 | Davison et al. |
| 5,324,299 A | 6/1994 | Davison et al. |
| 5,342,292 A | 8/1994 | Nita et al. |
| 5,380,274 A | 1/1995 | Nita |
| 5,405,318 A | 4/1995 | Nita |
| 5,409,498 A | 4/1995 | Braddock et al. |
| 5,505,693 A | 4/1996 | Mackool |
| 5,570,693 A | 11/1996 | Jang et al. |
| 5,596,991 A | 1/1997 | Tanaka |
| 5,762,066 A | 6/1998 | Law et al. |
| 5,772,627 A | 6/1998 | Acosta et al. |
| 5,800,448 A * | 9/1998 | Banko ..................... 606/169 |
| 5,873,873 A | 2/1999 | Smith et al. |
| 5,897,523 A * | 4/1999 | Wright et al. ............ 604/22 |
| 5,906,628 A | 5/1999 | Miyawaki et al. |
| 5,957,943 A | 9/1999 | Vaitekunas |
| 5,980,510 A * | 11/1999 | Tsonton et al. ........... 606/169 |
| 6,063,050 A * | 5/2000 | Manna et al. ............ 606/169 |
| 6,090,120 A * | 7/2000 | Wright et al. ............ 606/169 |
| 6,096,033 A * | 8/2000 | Tu et al. .................. 606/169 |
| 6,099,537 A * | 8/2000 | Sugai et al. ............. 606/205 |

\* cited by examiner

*Primary Examiner*—Eric F. Winakur
*Assistant Examiner*—David J. McCrosky
(74) *Attorney, Agent, or Firm*—Verne E. Kreger

(57) ABSTRACT

A therapeutic ultrasound instrument is described for cutting, dissecting, or cauterizing tissue. Ultrasonic vibrations, when transmitted to organic tissue at suitable energy levels and using a suitable end-effector, may be used for the safe and effective treatment of many medical conditions. An ultrasonic surgical instrument is described which incorporates an articulating shearing end-effector. The instrument comprises an ultrasonic transducer, an ultrasonically activatable end-effector, and a substantially solid ultrasonic waveguide that connects the ultrasonic transducer to the end-effector. The waveguide comprises a transmission section extending from the transducer to a fixed node, and an articulation section extending from the fixed node to a pivoting node. The end-effector includes a bifurcated waveguide segment. A handle is adapted to hold the transducer. An outer sheath extends from the handle to the end-effector and surrounds the waveguide. An actuation trigger is rotatably positioned on the handle, and an actuation arm extends from a distal end of the actuation trigger to the pivoting node. Such instruments are particularly suited for use in minimally invasive procedures, such as endoscopic or laparoscopic procedures.

6 Claims, 9 Drawing Sheets

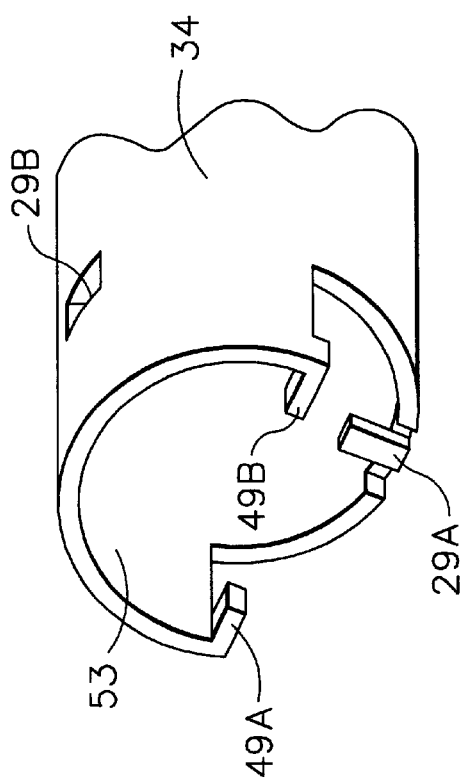
FIG. 5
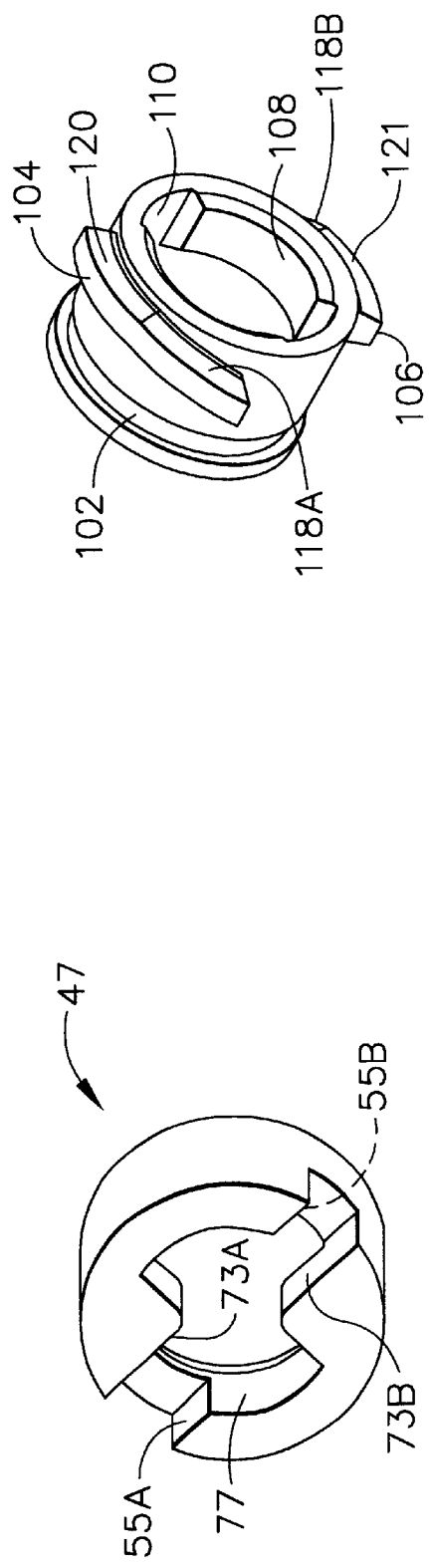
FIG. 7
FIG. 6

ARTICULATING ULTRASONIC SURGICAL SHEARS

RELATED APPLICATIONS

This application is a continuation-in-part of U.S. patent application Ser. No. 09/255,519 filed Feb. 22, 1999 now U.S. Pat. No. 6,090,102, which is a divisional of now issued U.S. Pat. No. 5,897,523.

FIELD OF THE INVENTION

The present invention relates, in general, to ultrasonic surgical instruments and, more particularly, to an articulating shearing end-effector for ultrasonic surgical instruments.

BACKGROUND OF THE INVENTION

This application is related to the following copending patent applications: application Ser. No. 08/770,550 filed Dec. 23, 1996 now U.S. Pat. No. 6,051,010; application Ser. No. 08/808,652 filed Feb. 28, 1997 now U.S. Pat. No. 5,589,275; application Ser. No. 09/255,519 filed Feb. 22, 1999 now U.S. Pat. No. 5,897,523; and application Ser. No. 09/464,567 filed Dec. 16, 1999; which are hereby incorporated herein by reference.

Ultrasonic instruments, including both hollow core and solid core instruments, are used for the safe and effective treatment of many medical conditions. Ultrasonic instruments, and particularly solid core ultrasonic instruments, are advantageous because they may be used to cut and/or coagulate organic tissue using energy in the form of mechanical vibrations transmitted to a surgical end-effector at ultrasonic frequencies. Ultrasonic vibrations, when transmitted to organic tissue at suitable energy levels and using a suitable end-effector, may be used to cut, dissect, or cauterize tissue.

Ultrasonic instruments utilizing solid core technology are particularly advantageous because of the amount of ultrasonic energy that may be transmitted from the ultrasonic transducer, through the waveguide, to the surgical end-effector. Such instruments are particularly suited for use in minimally invasive procedures, such as endoscopic or laparoscopic procedures, wherein the end-effector is passed through a trocar to reach the surgical site.

Solid core ultrasonic instruments adapted for use in surgery and, more particularly, for use in minimally invasive surgery, are well known in the art. For example, U.S. Pat. No. 5,322,055 illustrates an ultrasonic surgical shears that utilizes solid core ultrasonic technology, while U.S. Pat. No. 5,324,299 illustrates an ultrasonic hook blade end-effector for use in surgical applications. In addition, articulating instruments for use in minimally invasive surgery are also known in the art. For example, U.S. Pat. No. 5,409,498 describes an articulating endocutter for use in cutting and stapling tissue.

Many ultrasonic surgical instruments used for cutting and coagulation rely upon relatively stiff, solid core ultrasonic waveguides to efficiently deliver energy from the transducer to the end-effector. In such instruments it may be desirable to articulate the end-effector in order to provide the surgeon with flexibility in engaging hard to reach structures. However, the relatively stiff solid core ultrasonic waveguides and the limited structural space available in minimally invasive instruments make it difficult to design appropriate mechanisms for articulating end-effectors in such devices. One option, which is illustrated and described in U.S. patent application Ser. No. 08/770,550 previously incorporated herein by reference, involves separating the waveguide into two or more segments that may be moved independently to provide articulation.

Flexible high power ultrasonic surgical instruments are also available. Flexible ultrasonic surgical instruments such as atherosclerosis treatment devices, thrombolysis devices, or some stone crushing devices are typically thin wires encased in a polymeric sheath, are relatively flexible, and articulate if assisted with known flexible endoscopy articulation means. For example, U.S. Pat. No. 5,380,274 describes a flexible ultrasonic catheter, and U.S. Pat. No. 4,108,211 describes a flexible endoscope mechanism.

It would, therefore, be advantageous to design an articulating solid core ultrasonic surgical instrument wherein the ultrasonic waveguide is substantially continuous. It would further be advantageous to design a solid core ultrasonic surgical instrument wherein the end-effector was both rotatable and articulatable. It would further be advantageous to design an articulating solid core ultrasonic surgical instrument which could be passed through a trocar or other surgical access device and the end-effector could be articulated utilizing a handle positioned outside of the surgical access device. The present invention incorporates improvements to known ultrasonic surgical instruments to provide these advantages.

SUMMARY OF THE INVENTION

A surgical instrument comprising an ultrasonic transducer, an ultrasonically activatable end-effector, and a substantially solid ultrasonic waveguide which connects the ultrasonic transducer to the end-effector. The waveguide comprises a transmission section extending from the transducer to a fixed node, and an articulation section extending from the fixed node to a pivoting node. The end-effector includes a bifurcated portion. A handle is adapted to hold the transducer. An outer sheath extends from the handle to the end-effector and surrounds the waveguide. An actuation trigger is rotatably positioned on the handle, and an actuation arm extends from a distal end of the actuation trigger to the pivoting node wherein movement of the actuation trigger performs both articulation and actuation of the end-effector.

BRIEF DESCRIPTION OF THE DRAWINGS

The novel features of the invention are set forth with particularity in the appended claims. The invention itself, however, both as to organization and methods of operation, together with further objects and advantages thereof, may best be understood by reference to the following description, taken in conjunction with the accompanying drawings in which:

FIG. 5 is a perspective partial view illustrating the distal end of the actuating arm of a surgical instrument according to the present invention;

FIG. 6 is a perspective view illustrating a distal portion of the waveguide collar of a surgical instrument according to the present invention;

FIG. 7 is a perspective view illustrating a proximal portion of the waveguide collar of a surgical instrument according to the present invention;

DETAILED DESCRIPTION OF THE INVENTION

Figure 1:
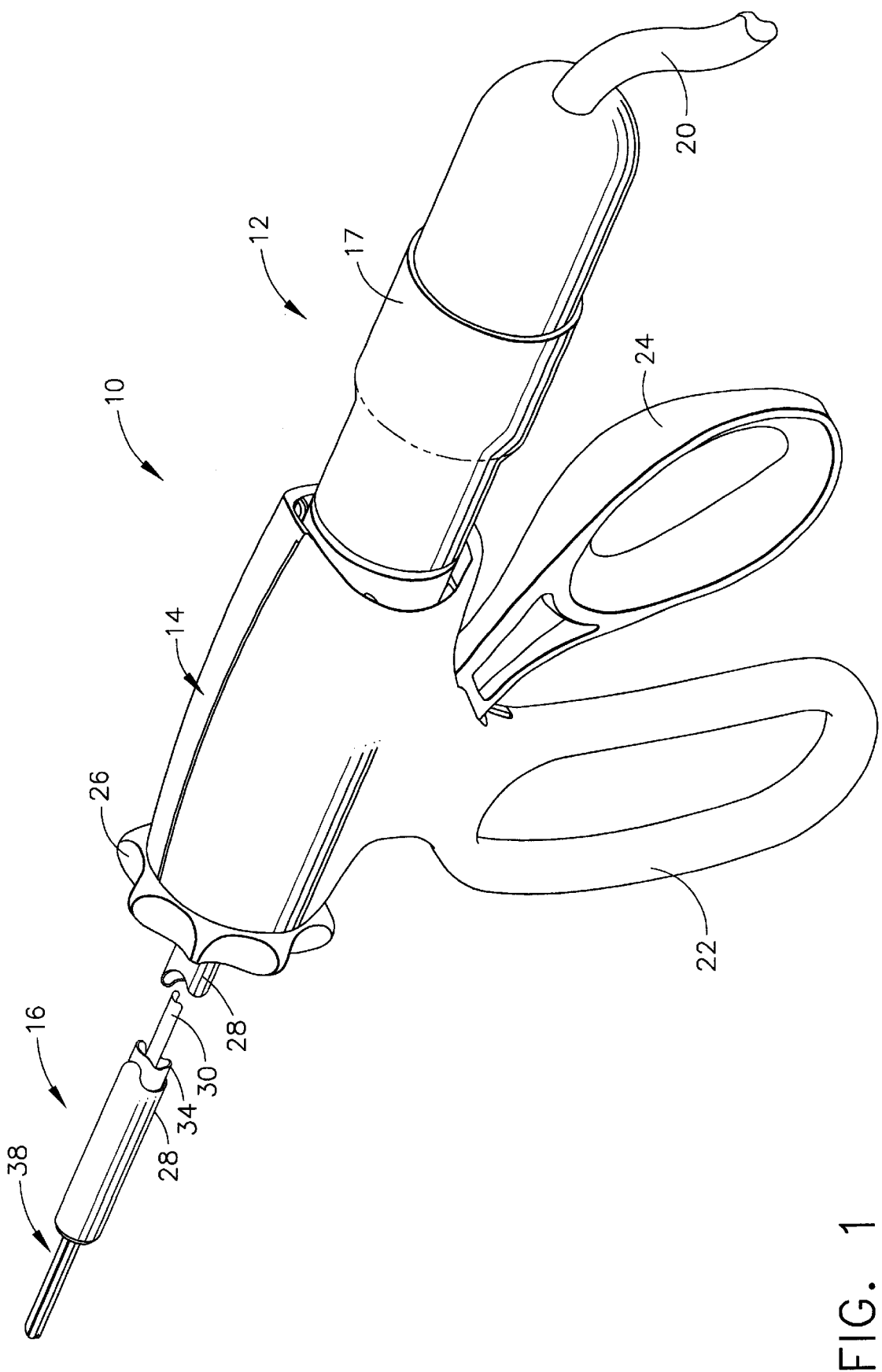
FIG. 1 is a perspective partial cutaway view illustrating a surgical instrument including an articulatable ultrasonic surgical shears according to the present invention, wherein the surgical instrument is illustrated in combination with an ultrasonic transducer.

FIG. 1 illustrates a surgical instrument 10 including an end-effector, designated as a shear blade 38 that may be both articulated and actuated according to the present invention. In FIG. 1, surgical instrument 10 is illustrated in combination with ultrasonic transducer 12. Surgical instrument 10 includes instrument handle 14, ultrasonic transmission rod assembly 16 and ultrasonic shear blade 38. Ultrasonic transducer 12 includes generator housing 17, which may also be referred to as a handpiece, and power supply cable 20. Ultrasonic transducer 12 houses transduction elements, preferably piezoceramic elements, for converting an electrical signal, for example, a 55,500 Hz sinusoidal waveform, into a mechanical longitudinal vibration. A suitable ultrasonic handpiece is available from Ethicon Endo-Surgery Inc. in Cincinnati Ohio as make ULTRACISION® and model HP051. Instrument handle 14 includes finger grip 22, actuation trigger 24 and rotation knob 26.

Figure 2:
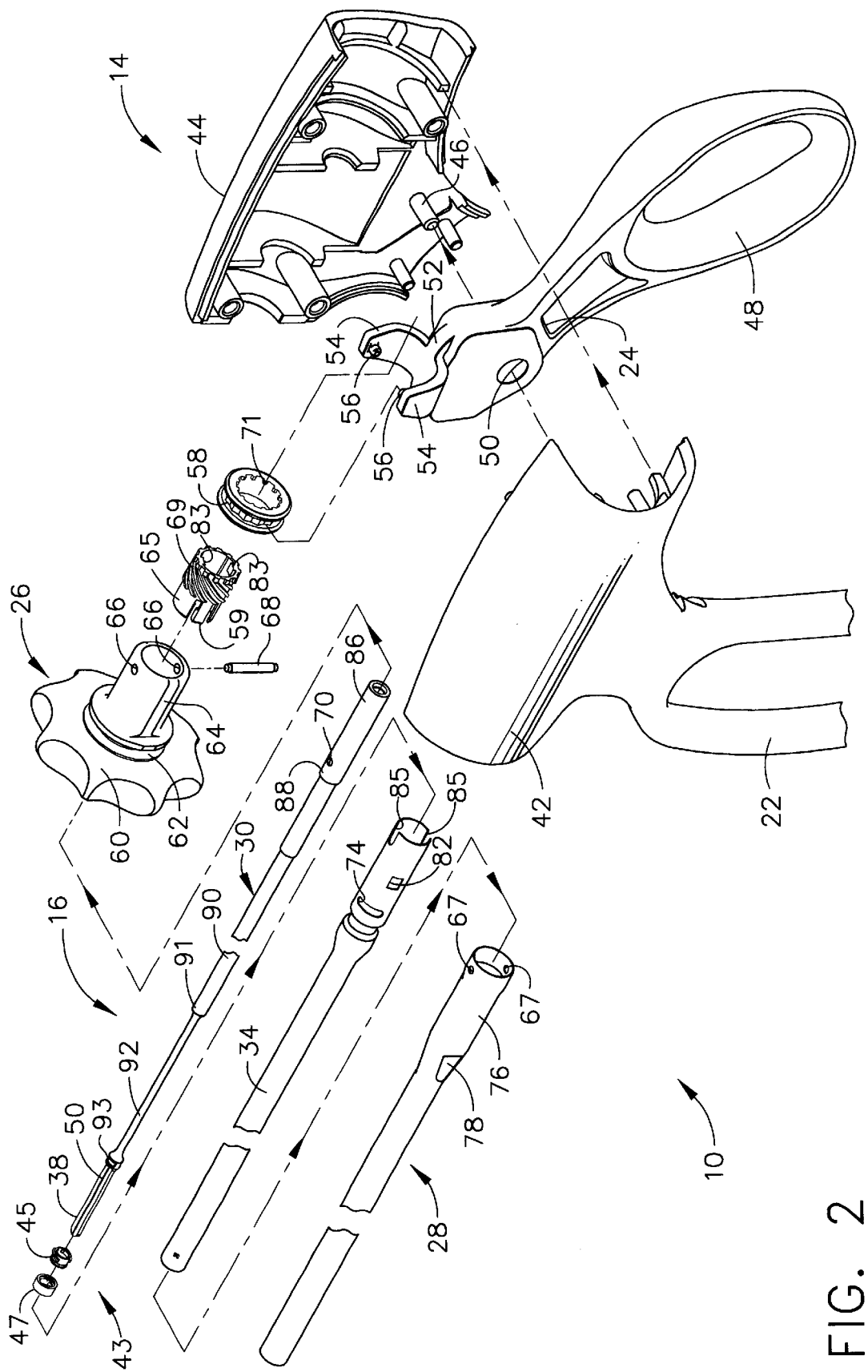
FIG. 2 is an exploded perspective view of a surgical instrument according to the present invention.

FIG. 2 illustrates the elements and interconnection of instrument handle 14, ultrasonic transmission rod assembly 16 and ultrasonic shear blade 38. Instrument handle 14 includes left housing half 42 and right housing half 44. Left housing half 42 includes finger grip 22. Actuation trigger 24 is rotatably mounted on pivot pin 46 between left housing half 42 and right housing half 44. Actuation trigger 24 includes thumb ring 48, pivot 50, yoke 52, yoke arms 54 and detent pins 56. Driver collar 58 is positioned in yoke 52 and rotatably engaged by detent pins 56. Driver collar 58 comprises drive teeth 71, engageable with drive threads 69 of rotation driver 65. Rotation knob 26 is rotatably positioned between left housing half 42 and right housing half 44 at the distal end of instrument handle 14. Rotation knob 26 includes rotation disk 60, rotation channel 62, rotation drive tube 64 and rotation knob connector pin holes 66.

In FIG. 2 ultrasonic transmission rod assembly 16 includes outer sheath 28, ultrasonic waveguide 30, and actuating arm 34. Outer sheath 28 is affixed to ultrasonic waveguide 30, actuating arm 34 and rotation drive tube 64 by rotation connector pin 68 which passes through rotation knob connector pin holes 66, waveguide connector pin hole 70, outer sheath connector pin holes 67, and actuation arm connector pin slot 74. Outer sheath 28 includes proximal tube 76, and wrench flats 78. Actuating arm 34 is positioned within and extends from the proximal to the distal end of outer sheath 28. Actuating arm 34 includes actuation arm connector pin slot 74 and actuation slot 82 at the proximal end. Actuation arm 34 is adapted to engage rotation driver 65 via keys 83 and keyways 85. Actuating arm 34 is positioned on ultrasonic waveguide 30 within outer sheath 28.

In FIG. 2 ultrasonic waveguide 30 includes node isolator 88, connector segment 86, transmission segment 90, pivoting node 93, shear blade 38, fixed node 91, and articulation segment 92. Articulation segment 92 is bounded by fixed node 91 at the proximal end thereof and pivoting node 93 at the distal end thereof. Pivoting node 93 is surrounded by waveguide collar 43 comprising an articulation collar 45 and an actuation collar 47. Articulation segment 92 is generally thinner than transmission segment 90 and, more particularly, preferably has a diameter of 20 to 70 percent of the diameter of the narrowest portion of transmission segment 90. In addition, or as an alternative, articulation segment 92 may include a bend or curve to facilitate rotational movement of pivoting node 93. Reducing the force required to bend articulation segment 92 facilitates rotation. Ultrasonic waveguide 30 is preferably fabricated from a solid core shaft constructed out of material which propagates ultrasonic energy efficiently, such as a titanium alloy (e.g., Ti-6A1-4V) or an aluminum alloy.

Figure 2A:
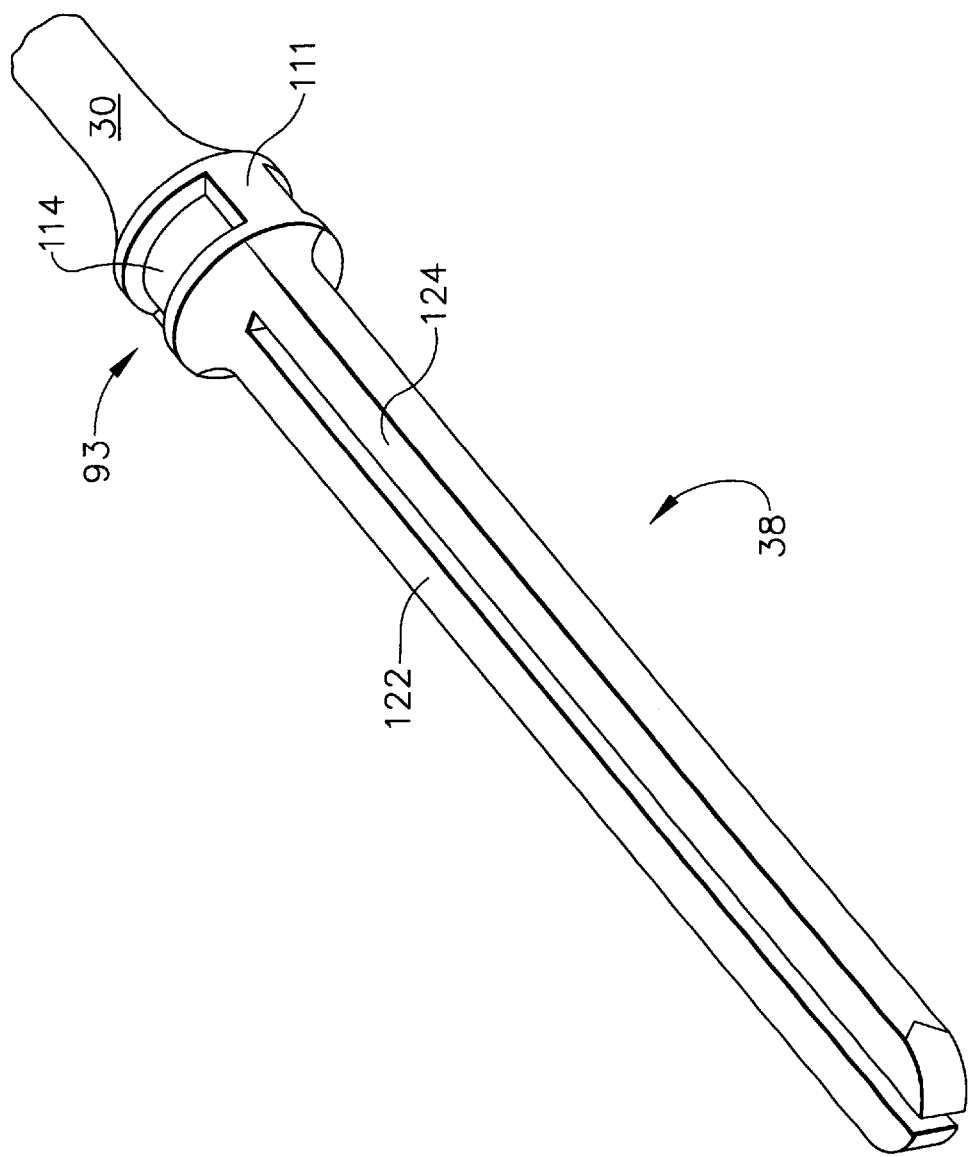
FIG. 2A is a perspective view of the distal end of the ultrasonic waveguide illustrated in FIG. 2.

FIG. 2A illustrates first arm 122 and second arm 124 extending from the distal portion of ultrasonic waveguide 30. First arm 122 and second arm 124 are bifurcated from ultrasonic waveguide 30 near pivoting node 93. This bifurcation may be accomplished by cutting the distal portion of ultrasonic waveguide 30 using a laser cutting tool, EDM machine, or other methods known in the art. During actuation of shear blade 38, first arm 122 and second arm 124 may be made to move normally to their length in a scissoring action, cutting any tissue therebetween.

Figure 3:
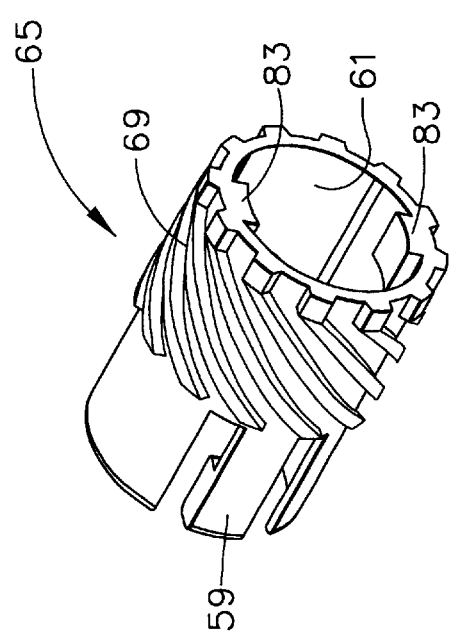
FIG. 3 is a perspective view of the rotation driver of the articulation and actuation mechanism shown in FIG. 4.

As illustrated in FIG. 3, rotation driver 65 includes drive threads 69, latch 59, and keys 83. Latch 59 is insertable into actuation slot 82 of actuating arm 34 (see FIG. 2). Threads 69 are angled along the length of rotation driver 65 to cause rotation driver 65 to rotate as driver collar 58 is moved forward over rotation driver 65 as further illustrated in FIG. 4.

Figure 4:
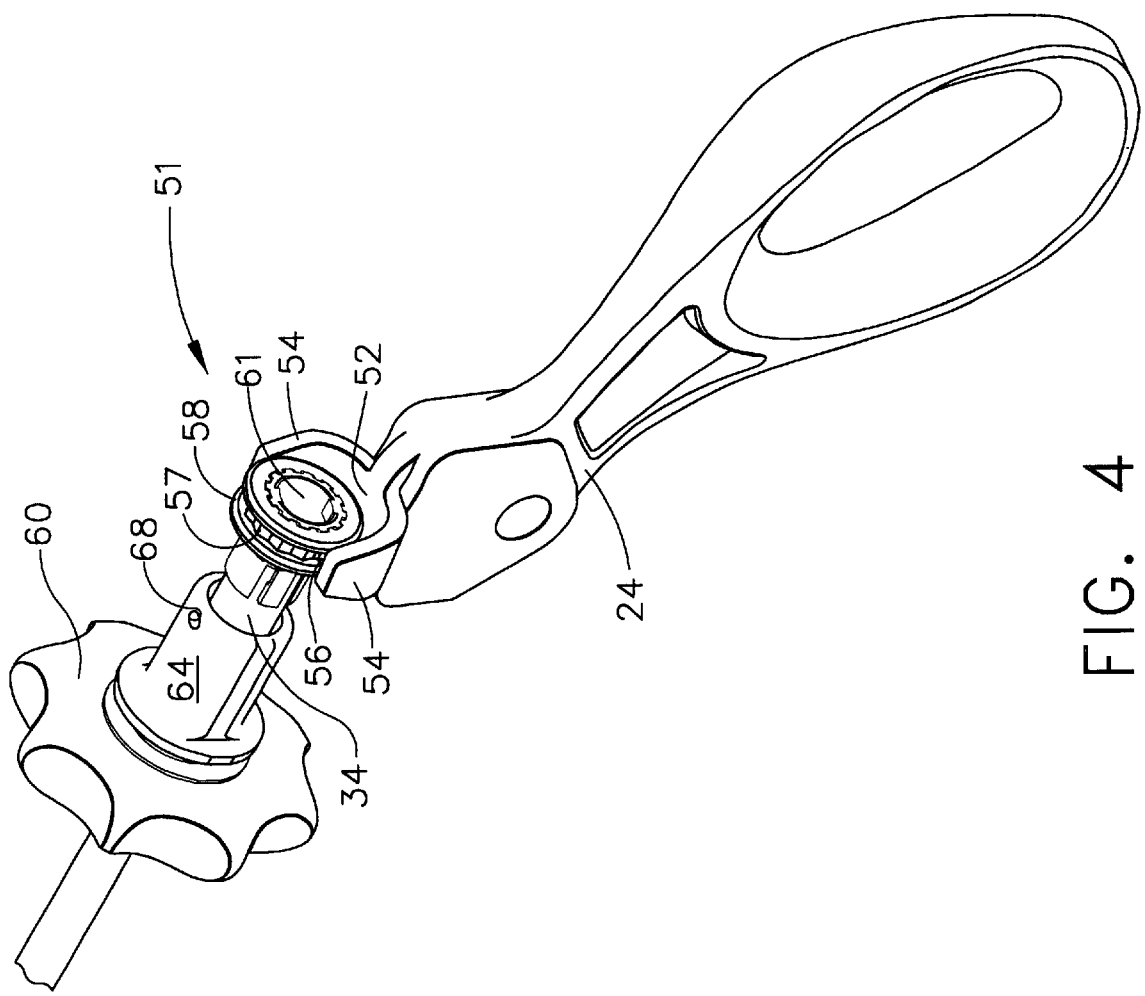
FIG. 4 is a perspective view of an actuation mechanism internal to the surgical instrument shown in FIG. 1.

FIG. 4 illustrates handle actuation mechanism 51 of surgical instrument 10. In handle actuation mechanism 51, actuation trigger 24 is pivotally connected to driver collar 58 by yoke 52. Yoke arms 54 of yoke 52 spring load detent pins 56 in collar rotation channel 57. The proximal end of ultrasonic waveguide 30 extends through central aperture 61 of rotation driver 65. The proximal end of actuating arm 34 extends into collar central aperture 61.

Referring to FIGS. 2 through 4, latch 59 of rotation driver 65 engages actuation slot 82 that is positioned at the proximal end of actuating arm 34. The proximal end of ultrasonic waveguide 30 is rotationally and axially affixed to rotation knob 26 by rotation connector pin 68 that passes through rotation drive tube 64. The proximal end of actuating arm 34 is rotatably affixed to rotation knob 26 by rotation connector pin 68 which passes through rotation drive tube 64 and actuation arm connector pin slot 74 of actuating arm 34. Drive teeth 71 of driver collar 58 engage drive threads 69 of rotation driver 65. As driver collar 58 is driven over rotation driver 65 by yoke 52, actuating arm 34 is rotated within outer sheath 28. Rotation of actuating arm 34 within outer sheath 28 may be independent of rotation of ultrasonic transmission rod assembly 16 as a whole.

FIGS. 5 through 11 illustrate how ultrasonic shear blade 38 is made to both articulate and shear through actuation of thumb ring 48 via handle actuation mechanism 51 (FIG. 4). In FIG. 5, the distal end of actuating arm 34 comprises thread tabs 29A and 29B and shear tabs 49A and 49B. Thread tabs 29A and 29B and shear tabs 49A and 49B may be formed from actuating arm 34 by processes such as, for example, cutting and forming the thread tabs 29A and 29B and shear tabs 49A and 49B from actuating arm 34. Actuating arm 34 also comprises an opening 53.

FIG. 6 illustrates the actuation collar 47 of the waveguide collar 43 of a surgical instrument 10 according to the present invention. Actuation collar 47 comprises tab faces 55A and 55B, contact lobes 73A and 73B, and a collar aperture 77. Collar aperture 77 accommodates ultrasonic shear blade 38 to be positioned within and extend from actuation collar 47.

FIG. 7 illustrates articulation collar 45, the proximal portion of the waveguide collar 43. Articulation collar 45 includes an attachment portion 102, articulation portions 104 and 106, bore 108, and keyway 110. Articulation collar 45 and actuation collar 47 are rotatably coupled, and work together to both articulate and actuate ultrasonic shear blade 38, as will be described below.

Figure 8:
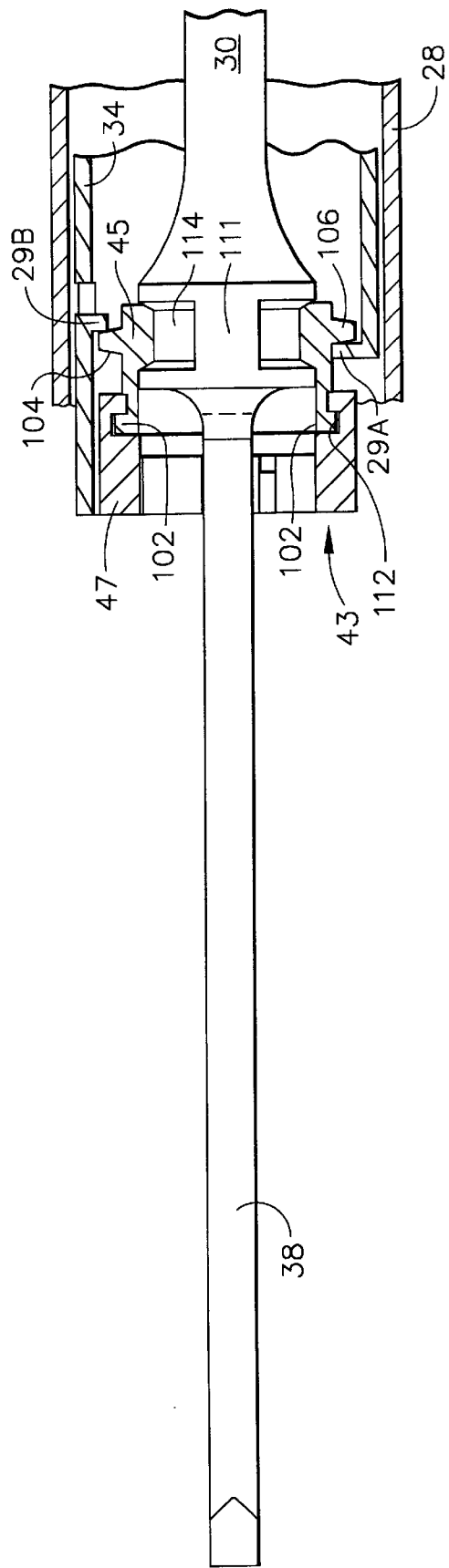
FIG. 8 is a side sectioned view sectioned through the articulation collar illustrating the ultrasonic waveguide surrounded by the articulation collar positioned within the inner-tube and outer-tube of the ultrasonic surgical shears in accordance with the present invention.

FIG. 8 illustrates the distal end of surgical instrument 10 showing ultrasonic shear blade 38 in a non-articulated and non-actuated condition. Shear blade 38 extends straight and longitudinally from ultrasonic waveguide 30. Ultrasonic waveguide 30 is located within actuating arm 34 by waveguide collar 43. Actuating arm 34 is located within outer sheath 28. Key 111 of ultrasonic waveguide 30 rigidly locates articulation collar 45 onto a nodal attachment point 114 of ultrasonic waveguide 30. Attachment portion 102 of articulation collar 45 is shown coupled to groove 112 of actuation collar 47. Articulation portions 104 and 106 are shown contacting thread tabs 29B and 29A respectively.

Figure 9:
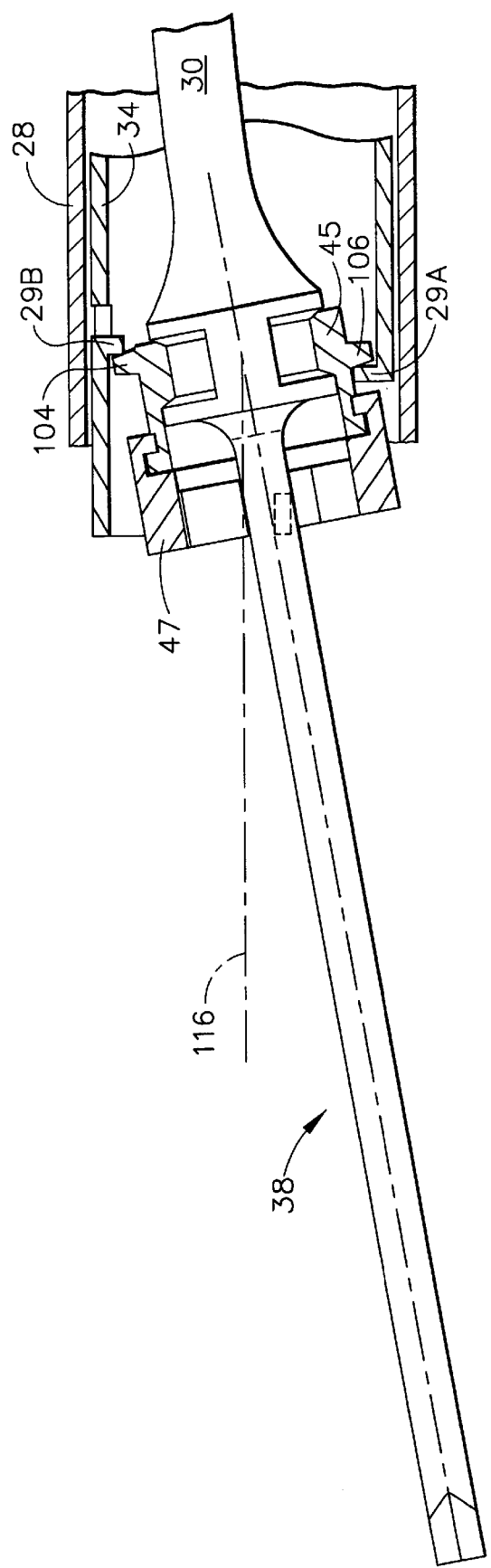
FIG. 9 illustrates the device of FIG. 8 in its articulated position.

As illustrated in FIG. 9, articulation of ultrasonic end-effector 38 is achieved by rotation of actuating arm 34 about ultrasonic waveguide 30. The distal end of surgical instrument 10 is illustrated with ultrasonic shear blade 38 in an articulated, but non-actuated condition. As thumb ring 48 is moved toward finger grip 22 (illustrated in FIG. 2), drive teeth 71 are pressed over drive threads 69, causing actuating arm 34 to rotate. Rotation of actuating arm 34 through the first (30) to (60) degrees articulates ultrasonic shear blade 38 (10) to (20) degrees from longitudinal axis 116. After (30) to (60) degrees of rotation, articulation portions 104 and 106 change from an angled region 118A and 118B to non-angled regions 120 and 121, as illustrated in FIG. 7. Articulation of shear blade 38 is accomplished by bending articulation segment 92 of ultrasonic waveguide 30 as described in U.S. patent application Ser. No. 09/255,519 previously incorporated herein by reference.

Figure 10:
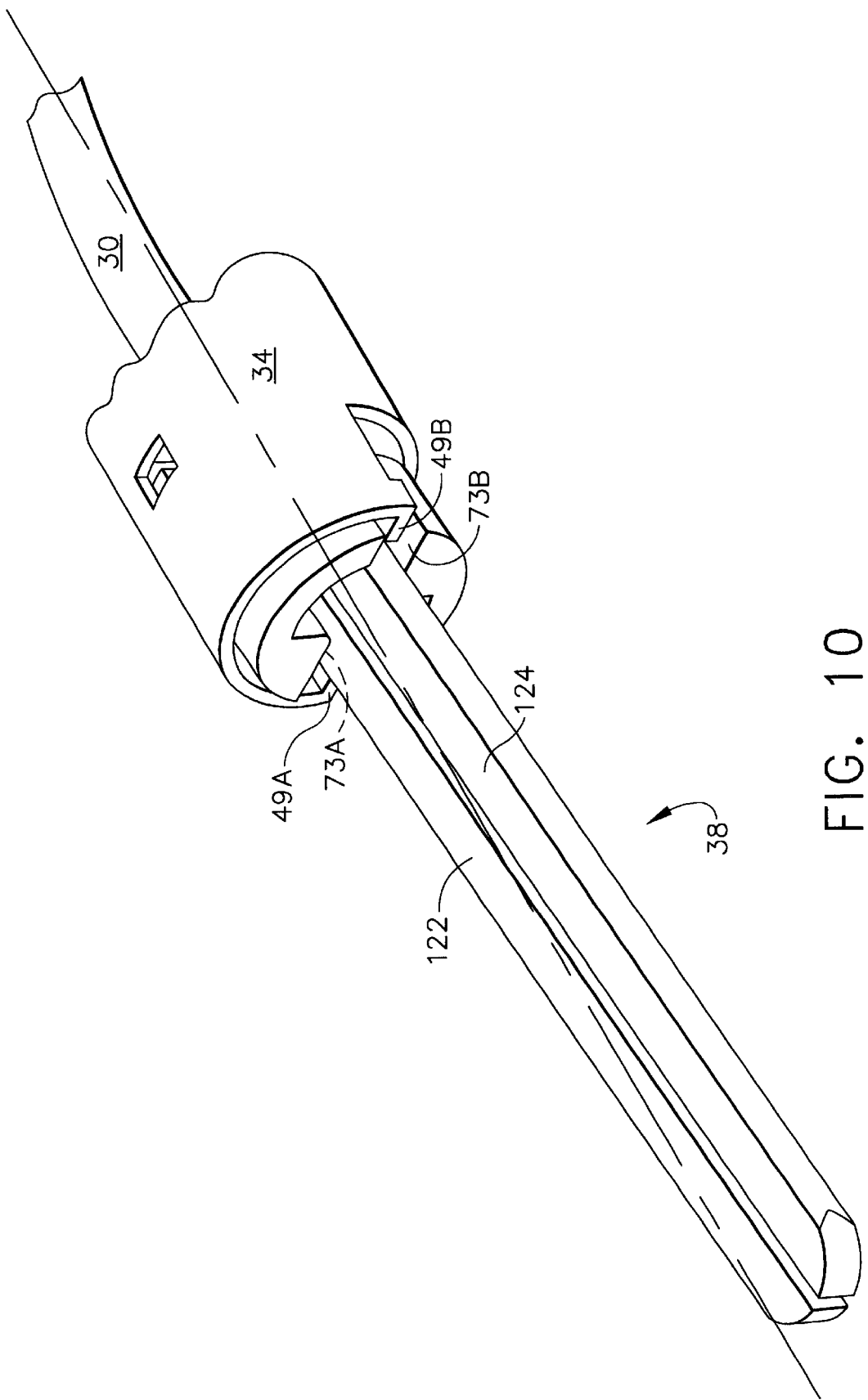
FIG. 10 is a cutaway perspective view illustrating a distal portion of the surgical instrument according to the present invention with the end-effector in the articulated position.

Now referring to FIGS. 2, 6, and 10, the actuation of shear blade 38 is illustrated. As actuating arm 34 continues to rotate past (30) degrees to (60) degrees, actuation collar 47 causes ultrasonic shear blade 38 to shear. Actuation collar 47 rotates freely with articulation collar 45 until shear tabs 49A and 49B contact tab faces 55A and 55B respectively. As rotation continues, contact tabs 73A and 73B apply a force to shear blade 38.

Figure 11:
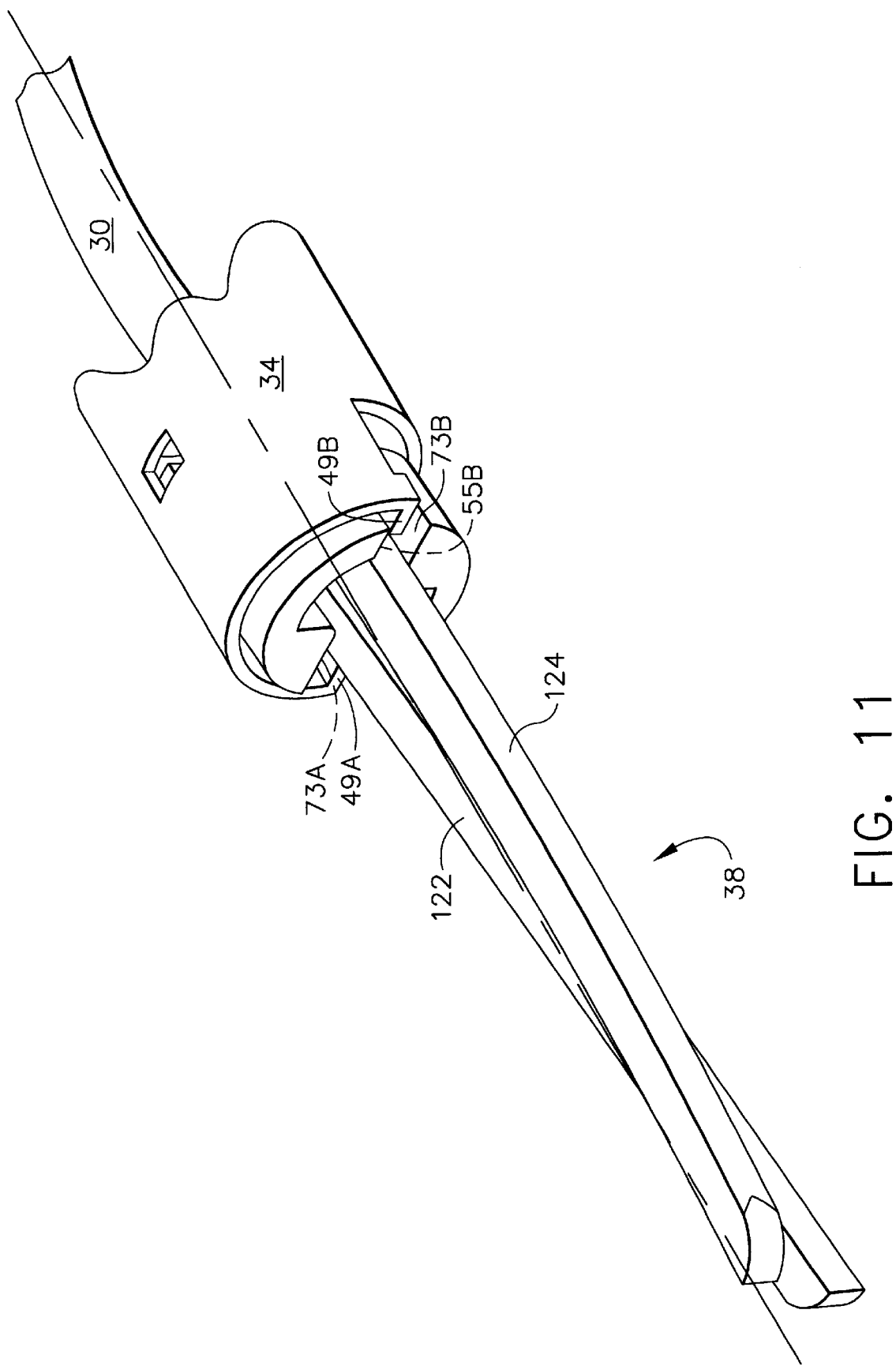
FIG. 11 illustrates the device shown in FIG. 10 with the end-effector in the articulated position and the end-effector sheared.

FIGS. 10 and 11 illustrate shear blade 38 moving from an articulated non-actuated state to an articulated actuated state. Shear tabs 49A and 49B contact tab faces 55A and 55B respectively and apply a force to shear blade 38 causing shear blade 38 to shear as illustrated in FIG. 11. During actuation, contact tab 73A forces first arm 122 in one direction, while contact tab 73B forces second arm 124 in the opposite direction causing shear blade 38 to shear. Counter-rotation of actuating arm 34 then allows first arm 122 and second arm 124 to return to their original non-actuated state.

Referring back to FIG. 2, shear blade 38 may be both articulated and actuated by moving actuation trigger 24 of instrument handle 14 toward finger grip 22. When actuation trigger 24 is moved toward finger grip 22, pivot 50 of actuation trigger 24 pivots on pivot pin 46, forcing yoke 52 to move toward the proximal end of instrument handle 14. Proximal movement of yoke 52 is transmitted to driver collar 58 by yoke arms 54 and detent pins 56 which engage rotation driver 65. Thus when actuation trigger 24 is moved toward finger grip 22, driver collar 58 is moved axially in a distal to proximal direction over rotation driver 65.

Axial movement of driver collar 58 is converted to rotation of rotation driver 65, that subsequently rotates actuating arm 34 by applying a force through latch 59 which engages actuation slot 82 in actuating arm 34. Actuation arm connector pin slot 74 in actuating arm 34 is elongated to ensure that rotation connector pin 68 and node isolator 88 do not interfere with the rotational movement of actuating arm 34. Thus, distal to proximal axial movement of driver collar 58 forces actuating arm 34 to rotate and, since rotation driver 65 is free to move with respect to the proximal end of ultrasonic waveguide 30, axial movement of actuating arm 34 does not result in axial movement of the proximal end of ultrasonic waveguide 30.

In order to properly position shear blade 38 prior to or after it is articulated, surgical instrument 10 is also adapted to allow shear blade 38 to be rotated around a central axis. Axial rotation of shear blade 38 is accomplished by moving rotation knob 26. When rotation disk 60 of rotation knob 26 is rotated, rotational force is transmitted through rotation drive tube 64 to rotation connector pin 68. As illustrated in FIG. 2, rotation channel 62 is mounted between left housing half 42 and right housing half 44 such that rotation knob 26 may be freely rotated but will not move axially with respect to instrument handle 14. Rotation connector pin 68 passes through rotation knob connector pin holes 66, outer sheath connector pin holes 67, mounting arm connector pin-slot 72, waveguide connector pin hole 70 and actuation arm connector pin slot 74, thus transmitting rotational forces from rotation knob 26 to outer sheath 28, ultrasonic waveguide 30 and actuating arm 34. Rotational forces are, in turn transmitted back to rotation driver 65 by the interconnection of actuation slot 82 and latch 59.

While preferred embodiments of the present invention have been shown and described herein, it will be obvious to those skilled in the art that such embodiments are provided by way of example only. Numerous variations, changes, and substitutions will now occur to those skilled in the art without departing from the invention. Accordingly, it is intended that the invention be limited only by the spirit and scope of the appended claims.

What is claimed is:

1. A surgical instrument comprising:
   a handle;
   a surgical end-effector, said surgical end-effector having a proximal end, a distal end, and a length;
   wherein said length from said proximal end of said surgical end-effector to said distal end of said surgical end-effector defines a longitudinal axis;
   said surgical end-effector further comprising a bifurcated portion, said bifurcated portion comprising:
   a first arm and a second arm;
   wherein said first arm and said second arm are moveable with respect to said longitudinal axis;

an elongated ultrasonic transmission rod assembly operatively coupled between said handle and said surgical end-effector, said elongated ultrasonic transmission rod assembly defining an instrument axis, wherein said transmission rod assembly comprises:

an ultrasonic waveguide transmission segment having a proximal end and a distal end;

a flexible ultrasonic waveguide segment having a proximal and a distal end, wherein said proximal end of said flexible segment is coupled to said distal end of said ultrasonic waveguide transmission segment and said distal end of said flexible segment is coupled to said surgical end-effector; and an actuating arm extending from said handle to said distal end of said flexible segment, wherein said actuating arm is operatively connected to said flexible segment and to said handle.

2. A surgical instrument according to claim 1 wherein said flexible segment is fixed at a said proximal end and rotatable at said distal end, wherein a rotation of said distal end of said flexible segment causes said longitudinal axis to deviate from said instrument axis.

3. A surgical instrument according to claim 1, wherein said rotation of said distal end causes deviation of said longitudinal axis from said instrument axis in a first range of rotation, and wherein a second range of rotation causes said first arm and said second arm to move with respect to said longitudinal axis.

4. A surgical instrument comprising:

an ultrasonic transducer having a distal end;

a handle including an actuation trigger;

an ultrasonic surgical end-effector;

an ultrasonic waveguide extending from said distal end of said ultrasonic transducer to said ultrasonic surgical end-effector;

an outer sheath extending from said handle to said distal end of said ultrasonic waveguide;

an articulation segment of said ultrasonic waveguide having a proximal end and a distal end;

an articulation collar operatively coupled to said actuation trigger and to said distal end of said articulation segment of said ultrasonic waveguide, said articulation collar comprising:

an articulation means for articulating said surgical end-effector; and an actuation means for actuating said end-effector.

5. An ultrasonic scissors apparatus comprising:

a housing;

an outer tube having a proximal end joined to said housing, and a distal end, said outer tube defining a longitudinal axis;

an inner tube rotatably positioned within said outer tube; and an ultrasonic waveguide positioned within said inner tube, said ultrasonic waveguide having an end-effector extending distally of said distal end of said outer tube, said end-effector initially positioned along said longitudinal axis;

wherein initial rotation of said inner tube causes said end-effector to deviate from said longitudinal axis.

6. An ultrasonic scissors apparatus in accordance with claim 5, wherein continued rotation of said inner tube actuates said end-effector.

* * * * *